United States Patent
Riff et al.

(10) Patent No.: US 7,366,570 B2
(45) Date of Patent: Apr. 29, 2008

(54) METHOD AND A SYSTEM FOR USING IMPLANTED MEDICAL DEVICE DATA FOR ACCESSING THERAPIES

(75) Inventors: Kenneth M. Riff, Orono, MN (US); Patrick M. Mahoney, Maple Grove, MN (US); Clifton W. Owens, Minnetonka, MN (US); Rahul Mehra, Stillwater, MN (US); Michael F. Hess, Minneapolis, MN (US); Nirav V. Sheth, Coon Rapids, MN (US); Nancy Perry Pool, Minnetonka, MN (US); Michael R. Ujhelyi, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 857 days.

(21) Appl. No.: 10/376,061

(22) Filed: Feb. 26, 2003

(65) Prior Publication Data
US 2003/0139785 A1 Jul. 24, 2003

Related U.S. Application Data

(63) Continuation of application No. 09/740,127, filed on Dec. 18, 2000, now abandoned.

(60) Provisional application No. 60/173,062, filed on Dec. 24, 1999.

(51) Int. Cl.
*A61N 1/08* (2006.01)

(52) U.S. Cl. .............................. 607/27; 607/59; 607/60

(58) Field of Classification Search ................ 607/4–5, 607/9, 14, 15, 32, 60, 1–2, 27, 59
See application file for complete search history.

(56) References Cited

U.S. PATENT DOCUMENTS

| | | | |
|---|---|---|---|
| 4,930,604 A | | 6/1990 | Schienda et al. |
| 5,269,301 A | * | 12/1993 | Cohen .......................... 607/6 |
| 5,311,449 A | * | 5/1994 | Adams .................... 340/10.51 |
| 5,330,513 A | | 7/1994 | Nichols et al. |
| 5,366,896 A | | 11/1994 | Margrey et al. |

(Continued)

OTHER PUBLICATIONS

Healtheon Company "Services and Solutions" Internet Printout: http://www.healtheon.com/services.index.html Printed Out Aug. 5, 1999 8:49 AM.

(Continued)

*Primary Examiner*—Mark Bockelman
*Assistant Examiner*—Eric D. Bertram
(74) *Attorney, Agent, or Firm*—Daniel G. Chapik

(57) ABSTRACT

A method and system facilitates the access by a patient of implanted medical device related data for patient participation in their own clinical care and therapy. In an example embodiment, the method includes establishing a communications link between an implanted medical device and a data processor via an implanted medical device interface. Access to a secured database is obtained via the implanted device data processor using a set of patient identification data. A query is then submitted via the data processor to the secured database in response to input patient diagnostic data. Data received from the secured database is then displayed for use in a patient evaluation.

28 Claims, 4 Drawing Sheets

U.S. PATENT DOCUMENTS

| | | | |
|---|---|---|---|
| 5,437,278 A * | 8/1995 | Wilk | 600/425 |
| 5,490,862 A * | 2/1996 | Adams et al. | 607/6 |
| 5,557,546 A | 9/1996 | Fukai et al. | |
| 5,693,076 A * | 12/1997 | Kaemmerer | 607/59 |
| 5,697,959 A * | 12/1997 | Poore | 607/32 |
| 5,713,350 A * | 2/1998 | Yokota et al. | 600/300 |
| 5,713,937 A * | 2/1998 | Nappholz et al. | 607/30 |
| 5,714,726 A | 2/1998 | Ketoviita | |
| 5,720,770 A * | 2/1998 | Nappholz et al. | 607/30 |
| 5,792,205 A * | 8/1998 | Alt et al. | 607/32 |
| 5,925,066 A * | 7/1999 | Kroll et al. | 607/3 |
| 5,999,851 A * | 12/1999 | White | 607/5 |
| 6,250,309 B1 | 6/2001 | Krichen et al. | |
| 6,363,282 B1 | 3/2002 | Nichols et al. | |
| 6,386,882 B1 | 5/2002 | Linberg | |
| 6,411,851 B1 | 6/2002 | Winkler | |
| 6,418,346 B1 | 7/2002 | Nelson et al. | |
| 6,442,433 B1 | 8/2002 | Linberg | |
| 6,497,655 B1 | 12/2002 | Linberg et al. | |
| 2001/0012955 A1 * | 8/2001 | Goedeke et al. | 607/27 |
| 2002/0026223 A1 | 2/2002 | Riff et al. | |
| 2002/0040234 A1 | 4/2002 | Linberg | |

OTHER PUBLICATIONS

"Healtheon Announces E-Commerce Agreement With Option Care" Press Release Santa Clara, California on Aug. 3, 1999. 3 PP.

"Healtheone and Promina Health System to Deploy Integrated Physician Informaiton Network" Press Release Santa Clara, California Jul. 6, 1999. 3 PP.

"USIS Mines for Gold in Electronic Health Records" *Card Technology* Jun. 1998, p. 41.

* cited by examiner

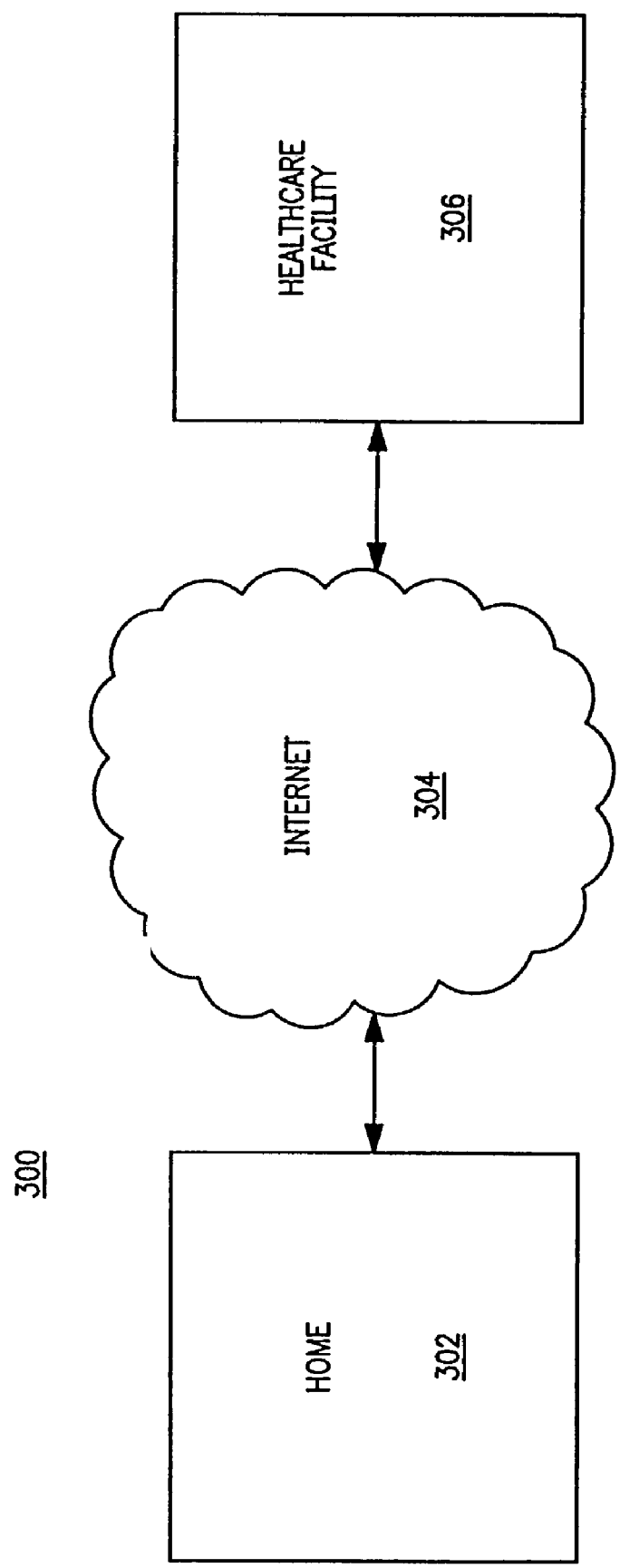

METHOD AND A SYSTEM FOR USING IMPLANTED MEDICAL DEVICE DATA FOR ACCESSING THERAPIES

RELATED PATENT DOCUMENTS

This application claims priority of U.S. application Ser. No. 09/740,127, filed Dec. 18, 2000 now abandoned and U.S. Provisional Application Ser. No. 60/173,062, filed on Dec. 24, 1999 (P-8857), entitled "Chronic Real-Time Information Management Systems for Implantable Medical Devices (IMDs)." The specification and drawings of the Provisional application are specifically incorporated herein in its entirety.

FIELD OF THE INVENTION

The present invention generally relates to a method and a system for using implanted medical device data to access medical data processing systems. Specifically, the invention relates to a method and a system for remotely accessing medical data processing systems adapted to provide implanted device therapies in response to patient diagnostic data received from an implanted medical device.

BACKGROUND OF THE INVENTION

The present invention is compatible and complementary with the elements disclosed in the following pending applications: "Medical System Having Improved Telemetry," filed Jul. 19, 1999, Ser. No. 09/356,340; "System and Method for Transferring Information Relating to an Implantable Medical Device to a Remote Location," filed on Jul. 21, 1999, Ser. No. 09/358,081; "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/429; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No 09/431,881 "Implantable Medical Device Programming Apparatus Having An Auxiliary Component Storage Compartment," filed Nov. 4, 1999, Ser. No. 09/433,477; "Remote Delivery Of Software-Based Training For Implantable Medical Device Systems," filed Nov. 10, 1999, Ser. No. 09/437,615; "Apparatus and Method for Remote Therapy and Diagnosis in Medical Devices Via Interface Systems," filed Dec. 14, 1999, Ser. No. 09/460,580; "Virtual Remote Monitor, Alert, Diagnostics and Programming For Implantable Medical Device Systems" filed Dec. 17, 1999, Ser. No. 09/466,284; "Instrumentation and Software for Remote Monitoring and Programming of Implantable Medical Devices (IMDs), filed Dec. 21, 1999, Ser. No. 60/172,937; "application Proxy For Telecommunication-enabled Remote Medical Access Instruments," filed Dec. 23, 1999, Ser. No. 60/173,081; "Information Network Scheme For Interrogation Of Implantable Medical Devices (IMDs)," filed Dec. 24, 1999, Ser. No. 60/173,064; "Medical Device GUI For Cardiac Electrophysiology Display And Data Communications," filed Dec. 24, 1999, Ser. No. 60/173,065; "Integrated Software System For Implantable Medical Device Installation And Management," filed Dec. 24, 1999, Ser. No. 60/173,082; "Dynamic Bandwidth Monitor And Adjuster For Remote Communications With A Medical Device," filed Dec. 24, 1999, Ser. No. 60/173,083 "Large-Scale Processing Loop For Implantable Medical Devices (IMDs)," filed Dec. 24, 1999, Ser. No. 60/173,079; "Chronic Real-Time Information Management Systems For Implantable Medical Devices (IMDs)," filed Dec. 24, 1999, Ser. No. 60/173,062; "Automatic Voice and Data Recognition For Medical Device Instrument Systems," filed Dec. 24, 1999, Ser. No. 60/173,071 "Central Switchboard to Facilitate Remote Collaboration With Medical Instruments," filed Dec. 24, 1999, Ser. No. 60/173,080; which are all incorporated by reference herein in their entireties.

A technology-based health care system that fully integrates the technical and social aspects of patient care and therapy should be able to flawlessly connect the patient with care providers irrespective of separation distance or location of the participants. While clinicians will continue to treat patients in accordance with accepted modern medical practice, developments in communications technology are making it ever more possible to provide medical services in a time and place independent manner.

Prior art methods of clinical services are generally limited to in-hospital operations. For example, if a physician needs to review the performance parameters of an implanted device, the patient will likely visit the clinic. If the medical condition of the patient with the implanted device warrants a continuous monitoring or adjustment of the device, the patient will have to stay in the hospital for an extended period of time. Such continuous treatment plans pose both economic and social hardship on patients. Depending on the frequency of data collection this procedure may seriously inconvenience patients that live in rural areas or have limited physical mobility. The need for upgrading the software of an implanted medical device also requires another trip to the hospital to have the upgrade installed. Further, as the segment of the population with implanted medical devices increases many more hospitals, clinics and service personnel will be needed to provide in-hospital care to patients, thus escalating the cost of healthcare.

Emergency trips to the hospital or clinic also increase the cost of healthcare due to lack of early detection of heart conditions, such as arrhythmias, that are treatable with less invasive practices such as medicinally, if the condition is detected on a timely basis. As the heart condition worsens, the need for physician intervention and long term hospitalization and medication increases. Current detectors of heart conditions, such as arrhythmia detectors, are available but these devices suffer from the shortcomings of external monitoring devices. The difficulties of patients to educate and inform themselves about medical devices prospectively or devices implanted in them, outside of the confines of the hospital, and to participate in their own clinical care and therapy by learning of the latest developments in this area are additional factors that contribute to the increasing costs of healthcare.

SUMMARY OF THE INVENTION

Various embodiments of the present invention are directed to addressing various needs in connection with reducing healthcare costs by facilitating the access of general and specific information on a patient's implanted medical device (IMD), thereby allowing the patient to participate in their own clinical care and therapy. Accordingly, the present invention provides a method and system for facilitating a patient's access to current IMD diagnostic data for timely administration of medical therapies with the assistance of an data processor.

In various embodiments the present invention supports a communications system for providing web-based data resources to capture, analyze, format and display patient-specific information on demand and in real-time. In addition, the invention provides an Internet-based secure site to enable a patient to uplink their IMD to transfer data into a data management center where the data is analyzed and relevant therapy/clinical care is dispensed accordingly. Another aspect of the invention pertains to arrhythmia management via a programmable patient arrhythmia notification device in coordination with the patient's IMD. The notification device can also communicate with a web-based remote data management center. In another aspect of the invention, IMD patients have access to a web-based data management system for IMDs for accessing various clinical and therapy alternatives and related information/services.

According to one embodiment of the invention, a method and system facilitates the access by a patient of implanted medical device related data for patient participation in clinical care and therapy. The method includes establishing a communications link between an implanted medical device and a data processor via an implanted medical device interface. Access to a secured database is obtained via the implanted device data processor using a set of patient identification data. A query is then submitted via the data processor to the secured database in response to input of patient diagnostic data. Data received from the secured database is then displayed for use in a patient evaluation.

According to another embodiment of the invention, a method and system facilitates access by an IMD patient to their own IMD diagnostic data for patient education and evaluation. The method includes establishing a communications link between an implanted medical device and a data processor via an implanted medical device interface. Access to a secured database is obtained via the data processor by using a set of patient identification data. Further, a set of patient diagnostic data from the implanted medical device is then transmitted to the data processor for processing. A set of formatted data is then generated, as a function of a data request from the patient, via the data processor using the patient diagnostic data. The set of formatted data received from the secured database via the data processor is then displayed for use in a patient evaluation regimen as required by the doctor or established medical care.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 3 is a diagram of a system for accessing and processing IMD information as a function of an IMD patient's request in accordance with an example embodiment of the invention.

Figure 1A:
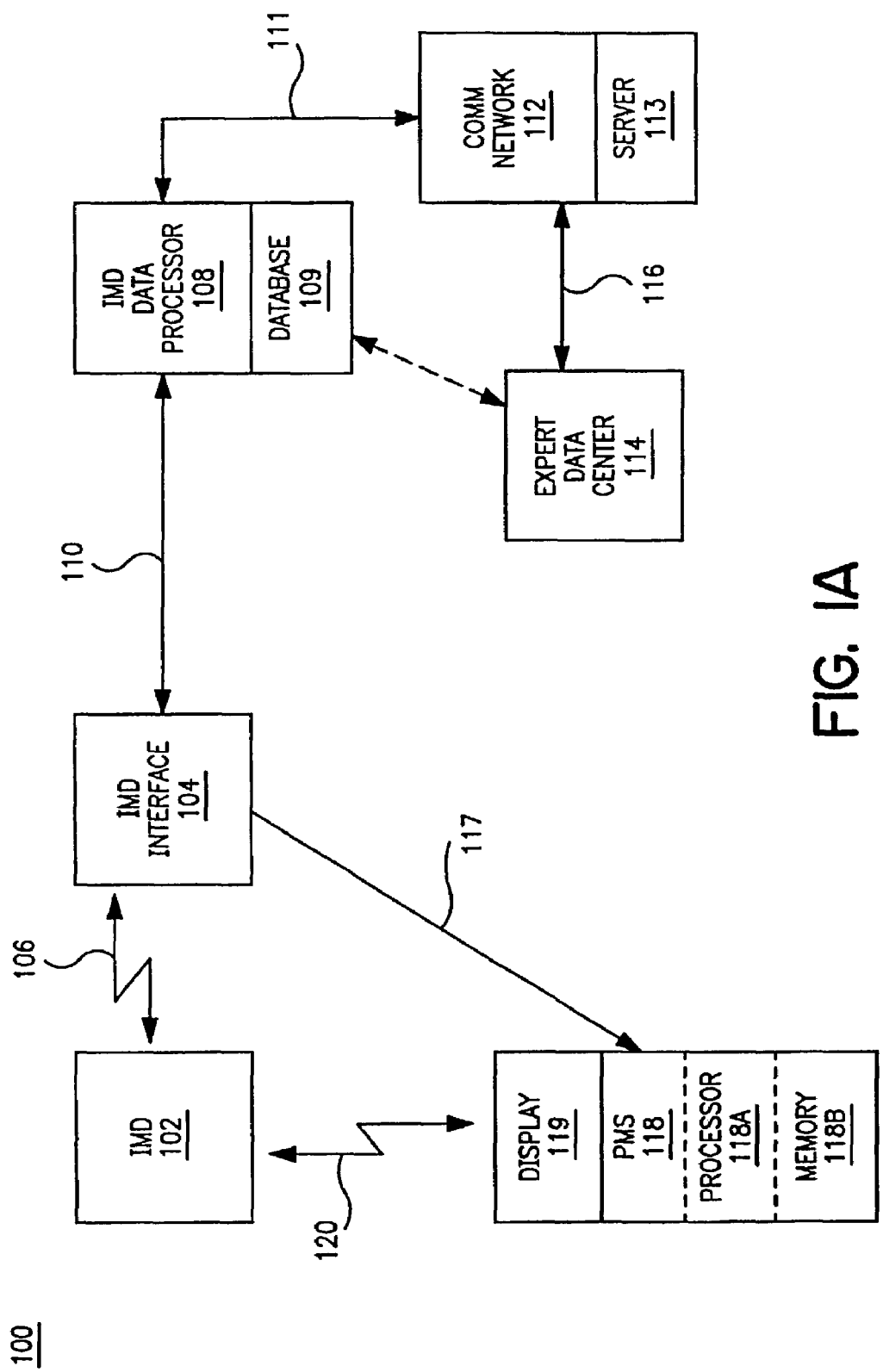
FIG. 1A illustrates a block diagram of a system for facilitating the access by an IMD patient to a data processor capable of processing IMD related data in accordance with an example embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a method and system for generating an IMD related data response as a function of a detected condition in connection with a patient's IMD. While the present invention is not necessarily limited to such an application, the invention will be better appreciated using a discussion of example embodiments in such a specific context.

Early patient notification of various heart conditions can empower a patient to take direct action regarding management of the identified heart condition. In the case of arrhythmias, a device guided antiarrhythmic therapy would allow patients to use drug therapy based upon implanted device notification rather than having to seek medical attention for recurring arrhythmic events. One of the capabilities provided by the present invention is that of arrhythmic detection with programmable notification tailored to specific drug therapies. Accurate detection of atrial fibrillation is a component of a properly operating patient notification device and IMD therapy implementation system.

In an example embodiment, an external messaging system is provided and adapted to communicate with an IMD and use an alpha-numeric messaging program to instruct the patient when to schedule drug therapy. A configurable treatment process is incorporated into an arrhythmia monitoring and notification system for guiding medication therapy for arrhythmia termination, fast ventricular response, or anticoagulation therapy. The configurable features cooperate with the external messaging circuit to assist in scheduling or rescheduling therapy based on patient action and drug delivery timing. The process also provides closed loop communications between an implantable drug delivery system and an implanted electrical therapy device. The system of the present invention greatly simplifies the patient's role in the decision loop for self-administration of IMD therapies.

Referring now to the figures, FIG. 1A illustrates a block diagram of a system 100 for facilitating the access by a patient to an implanted medical device data processor that is capable of detecting various conditions in accordance with an example embodiment of the invention. System 100 facilitates the access by a patient to implanted medical device related data for the patient's participation in clinical care and therapy. System 100, in this example, includes an IMD port interface 104 that is coupled to an IMD 102 via a communications link 106. Communications link 106 is established, in this example, via telemetry when port interface 104 is in close proximity to the IMD. The link can also be established, for example, with radio frequency signal based telemetry. IMD interface 104 includes features of a programming head or wand that is incorporated into a programming unit for detecting and transmitting IMD diagnostic data. In another embodiment, IMD interface 104 includes an IRM (Interactive Remote Monitor) that is used to uplink data from the implanted device to IMD data processor 108 or to a related website. IMD port interface 104 is coupled via communications link 110 to an IMD data processor 108, which includes a database 109. Communications link 110 can be established via a telephone, a video conference call, a cellular telephone, via a separate Internet connection or other related communications formats for the transmission of data and voice to IMD data processor 108. IMD data processor 108 is coupled via a communications link 111 to a communications network 112, which includes a server 113. Network 112 is in turn coupled to a data processing center 114 via a communications link 116. The data processing center includes medical personnel that analyze and evaluate diagnostic data received from an IMD. The data processing center may be co-located with the patient or may be located remote from the patient and accessed through communications network 112.

In this example embodiment, a patient messaging system (PMS) 118, co-located with IMD 102 is coupled to IMD data processor 108 via IMD interface 104. PMS 118 includes a display 119 and a circuit adapted to assess and detect heart conditions in conjunction with the IMD. The circuit includes a processor 118A and a memory arrangement 118B as well as an audio signal arrangement (not shown) for emitting sounds that are audible by a patient having IMD 102. A similar circuit is also within data processor 108 for remote detection of heart conditions. In one example embodiment, PMS 118 is coupled to IMD 102 via a telemetry link 120 and is adapted to access IMD status information and independently alert the patient of a heart condition that requires some form of therapy or treatment. The patient is then advised of the therapy options available for treating the detected condition. In another embodiment, the patient initiates a patient query to determine IMD status. In both embodiments, PMS 118 generates at least one suggested therapy (medicinal and/or electrical pulse) that is displayed on display 119 and that is be exercised or administered primarily by the patient. In yet another embodiment, PMS 118 is also capable of programming or reconfiguring certain program features within IMD 102.

System 100 of the present invention provides the capabilities of notifying a patient of an arrhythmia onset and guiding the patient and/or physician to administer the appropriate drug or electrical therapy. By using PMS 118, which in this example is an alphanumeric messaging and programmable patient notification device, the patient is guided through various pharmacological and electrical therapies as required. The patient can now critically time the taking of medications to terminate an arrhythmic event or slow down the ventricular rate or use the medication in combination with electrical therapies. The longer the arrhythmia duration, the less successful medications will be in terminating the arrhythmia. In addition, anticoagulation drug therapy may have to be extended for an additional 3-4 weeks to reduce the risk of a stroke to the patient. Notification via PMS 118, which is proximate to IMD 102 (via a wrist worn device or a personal digital assistant type device), is useful in guiding the patient through anticoagulation therapy when events are long lasting and unresponsive to medical and/or electrical therapies. System 100, via PMS 118, provides the feature of advising the patient in real time of the success or progress of the elected treatment or therapy. Furthermore, since some medications can increase the likelihood that antitachycardia pacing or defibrillation therapies will terminate an arrhythmia, PMS 118 will guide the patient as to the appropriate time to take certain medication in order for electrical therapies to be more successful.

Referring again to FIG. 1A, a communications link is first established between IMD 102 and IMD data processor 108 via IMD port interface 104. In a related embodiment, the communications link is established directly between the IMD and data processor 118A in order to establish two way communications between the patient and PMS 118 for the patient implemented therapies scenario. Implanted medical device database 108, which is a secured database or website provided via IMD data processor 108, is then accessed by using a set of patient identification data. In this example embodiment, the patient identification data is the serial number of the IMD but can be a special code that is assigned to the IMD patient for obtaining access to the secured database. System 100 facilitates access by the patient having IMD 102 of the secured database using the IMD serial number as the password, after which the patient requests information and/or data from the database. Information available to the patient includes, but is not limited to, information about the particular IMD in use, latest technological developments, clinical trials, patient/lifestyle guidelines, support group information, special HOT LINE numbers for emergencies, dietary and exercise programs and additional links to other websites. System 100 detects the condition at the IMD patient location that the patient is seeking information or data and proceeds to provide the data as a function of the inquiry made. The data response is then generated by IMD data processor 108 and displayed (e.g., on a CRT or LCD screen or LED display) for use by the patient in educating himself on current IMD health concerns or issues.

In another example embodiment, processor 118A communications with the patient is initiated by either the patient or by PMS 118 where a heart condition is detected. In this example, the patient of IMD 102 actively seeks a status evaluation of (or a treatment strategy for) his IMD with respect to his heart and either activates PMS 118 or obtains access to IMD data processor 108 for an evaluation or detection of at least one of a plurality of current heart conditions. Once the link with the IMD data processor 108 (or PMS 118) is established, patient diagnostic data is uplinked to the IMD data processor (or PMS 118) for evaluation and detection of the patient's heart condition. Detectable heart conditions include, but are not limited to, arrhythmia, tachycardia, bradycardia and eventual heart failure and are detected over IMD port interface 104 for processor 108 (or directly by 118A from the IMD). A data response as a function of the detected heart condition is then generated by IMD data processor 108 (or PMS 118) and is displayed for use in patient evaluation. In an example embodiment, the data response is displayed on display 119 of PMS 118 and includes a list of recommended medicinal and/or electrical impulse therapies that are administered by the patient (or a medical assistant).

Figure 1B:
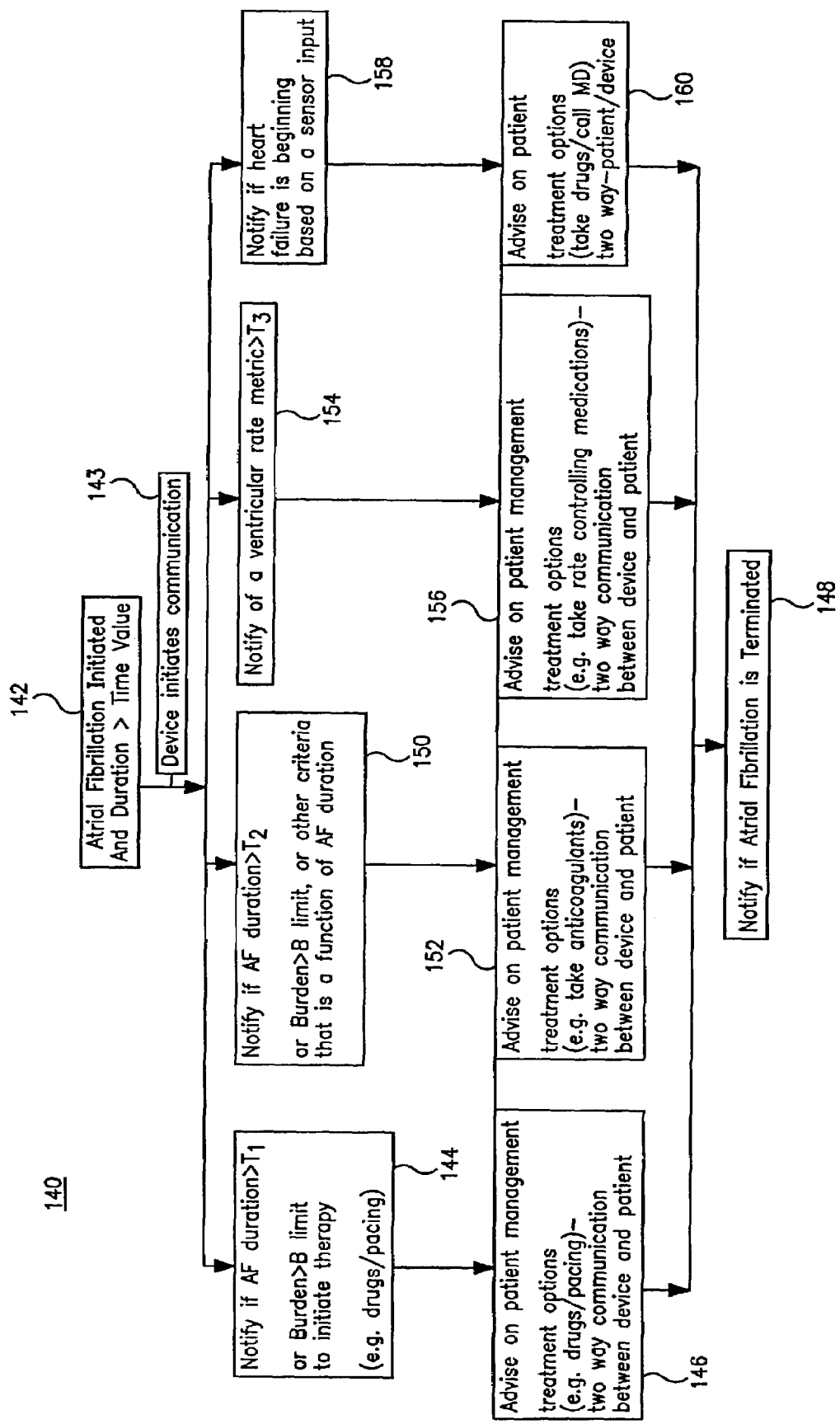
FIG. 1B is a flow diagram illustrating an example manner of implementing therapies in connection with detected heart conditions in accordance with an example embodiment of the invention.

Referring now to FIG. 1B, a flow diagram 140 illustrates an example manner of processing IMD diagnostic data and implementing therapies in connection with detected heart conditions, in accordance with an example embodiment of the invention. In general, the system guided drug therapy process is illustrated is programmable and is intended to interact and communicate with external messaging systems. In a related embodiment, a patient activator (not shown) communicates with PMS 118 to properly time electrical therapies with medication therapies. In this example embodiment, at step 142 atrial fibrillation (AF) is initiated or commences and lasts for a certain duration of time, with the time value exceeding a predefined time value before the patient notification process starts or before the patient notices that a problem may be occurring. At step 143 PMS 118 initiates communication with the patient, and depending on the time duration or other defined criteria, will follow either steps 144, 150, 154 or 158. At step 144, PMS 118 advises patient that AF has exceeded a time value of T1 and/or that the Burden has exceeded a certain Burden limit value (B limit) and that it is time to initiate therapy. In this example, the patient is alerted by an alarm signal coming from PMS 118 and is instructed at step 146, via an alphanumeric message on display 119, as to his treatment options. In this example, his treatment options include either drugs or pacing options or a combination of both. Two way communications already having been established as discussed earlier, the patient exercises one of the treatment options and advises PMS 118 of the treatment option exercised. At step 148, PMS 118 notifies the patient whether AF has terminated. If AF has not terminated, the process can loop back to step 144 or move to another step in process 140.

At step 150, the patient is notified by PMS 118 that the time duration has exceed a time value of T2, or a burden limit (or any other criteria that is a function of AF duration). At step 152, the patient is advised on patient management treatment options, which in this example includes taking anticoagulant medication. The patient again proceeds to exercise one of the treatment options and advises PMS 118 of the option exercised. As in the example described above, the process moves to step 148 where the patient waits to be notified that AF has terminated.

At step 154, PMS 118 notifies the patient that the ventricular rate metric has exceeded a time value of T3. At step 156, the patient is advised on patient management treatment options, which in this example includes taking rate-controlling medication. The patient again proceeds to exercise one of the treatment options and advises PMS 118 of the option exercised. As in the example described above, the process moves to step 148 where the patient waits to be notified that AF has terminated.

At step 158, PMS 118 notifies the patient that heart failure is beginning due to a prolonged AF condition. In one example, a sensor input that detects heart failure communicates the condition to PMS 118 in order that the patient is alerted of this condition. At step 160, the patient is advised on patient management treatment options, which in this example includes taking medication to control on the onset of heart failure and/or to call his physician immediately. The patient again proceeds to exercise one of the treatment options and advises PMS 118 of the option exercised. As in the example described above, the process moves to step 148 where the patient waits to be notified that AF has terminated. In all of the embodiments described, the patient has the choice of taking control of his own therapy with the guidance and regular feedback (via two-way communication) of PMS 118.

Figure 2:
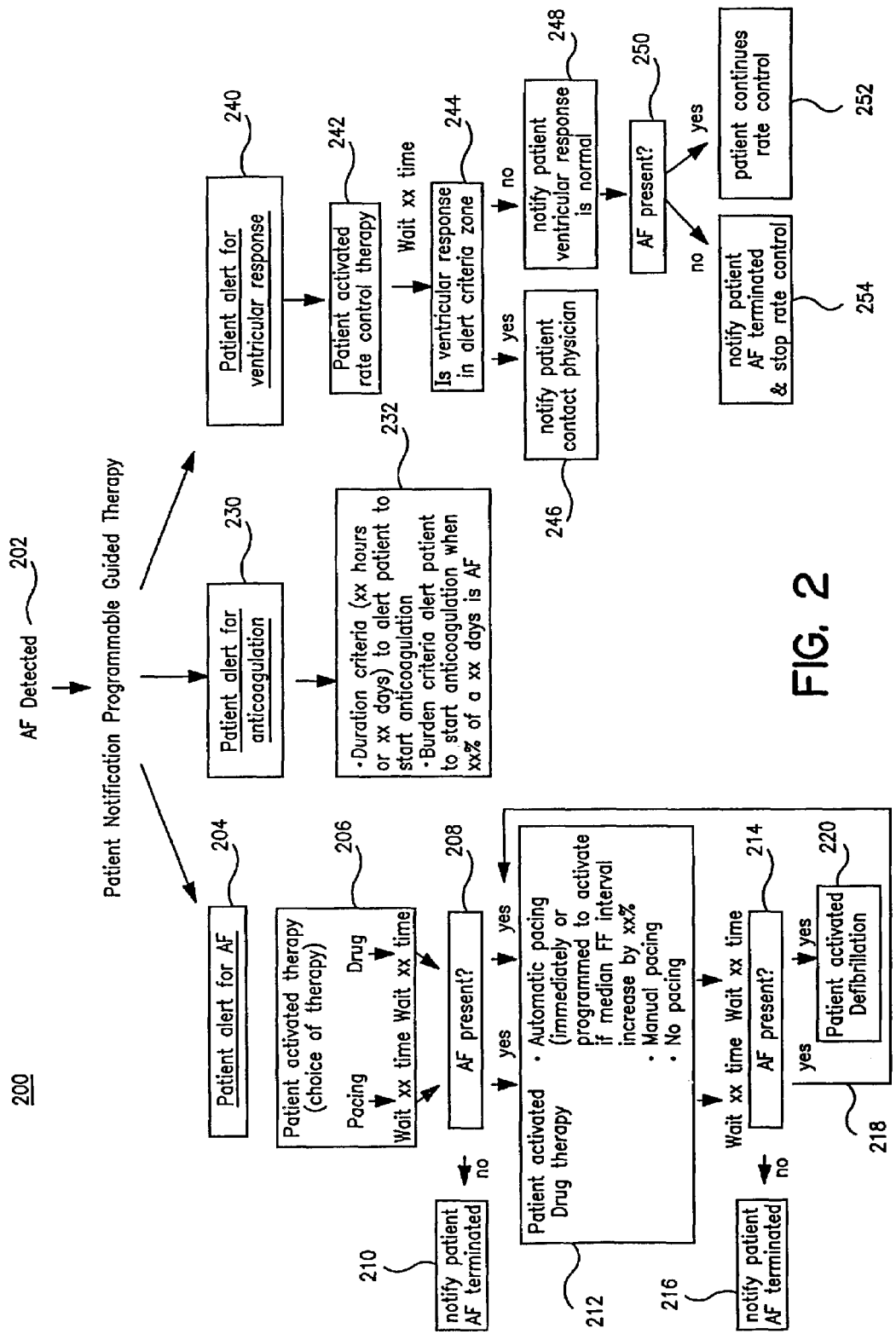
FIG. 2 is a flow diagram illustrating another manner of accessing IMD diagnostic data and implementing therapies in connection with detected heart conditions in accordance with another example embodiment of the invention.

Referring now to FIG. 2, a flow diagram 200 illustrates another manner of accessing and processing IMD diagnostic data, and implementing therapies in connection with detected heart conditions, in accordance with an example embodiment of the invention. At step 202, IMD data processor 108 (or processor 118A of PMS 118) detects an atrial fibrillation and the patient is notified by an audible sound emitted by PMS 118. In another example embodiment, the audible sound is prompted by a notification signal 117 sent by IMD data processor 108 via interface 104 to PMS 118. In this example embodiment, the patient of IMD 102 is advised of the detection of one of three conditions: patient alert for Atrial fibrillation (AF; step 204); patient alert for anticoagulation (step 230); and patient alert for rapid and prolonged ventricular rate (step 240). Depending on the detected condition, a different path is followed by the IMD patient in administering therapy with the assistance of PMS 118 and system 100. In one example, the patient is notified via PMS 118 to take a medication 206 and to advise PMS 118 when the medication has been taken. At step 208, a determination is made whether the AF is still present. If not, at step 210 the patient is notified that AF is terminated. If so, at step 212 the patient is advised accordingly and another set of therapy options is communicated to the patient. Depending on the programming of PMS 118, antitachycardia pacing will be automatically delivered at an optimal drug rate, which is set by either a fixed time interval or by a change in sensed atrial cycle length (a surrogate of drug effect). At step 214, another determination is made whether the AF is still present; if not, at step 216 the patient is advised accordingly. If so, at step 218 either automatic pacing continues with a return path to 212, or the patient, at step 220, activates the defibrillation mode of IMD 102 and applies a shock to terminate the arrhythmia.

In another embodiment, programmable PMS 118 instructs the patient to perform electrical therapies in order to terminate the arrhythmia. If this approach is not successful PMS 118 advises the patient to follow another course of action by taking the medication and activating PMS 118 to repeat the pacing therapies after a fixed time interval or when atrial cycle length changes. Shock therapy may be in order at this point with notification being programmed for a fixed time interval to allow the medication ample time to terminate the heart condition before having to provide the shock treatment. In most of the embodiments, the patient has the option of receiving continuous feedback via PMS 118 (or other display methods) regarding medication efficacy.

Referring to step 230 of FIG. 2, system 100 along with PMS 118 is helpful in assisting in the management of anticoagulation therapy. At step 232, the programmable features of PMS 118 have a burden threshold. For example, if atrial arrhythmia is present for greater than a certain portion of a 24- hour interval, the patient is notified to start anticoagulation therapy and/or see a physician.

Referring to step 240, system 100 assists in the management of ventricular rate control for patients with paroxysmal AF. PMS 118 and system 100 provide guidance in the use of medication only when needed, since rate controlling medications are poorly tolerated. This treatment strategy greatly improves a patient's quality of life by using the programmable feature of PMS 118; at step 242, to intermittently use rate control medications. At step 244, a determination is made whether the ventricular response is in the alert criteria zone, such as a fast zone. If so, at step 246 the patient is notified via the alert feature of PMS 118 that an AF is occurring (ventricular response is in the fast zone) and to start taking the rate control medication. If the ventricular response is not in the criteria zone, at step 248 the patient is notified that the ventricular response is normal. At step 250, another determination is made whether AF is present. If so, at step 252 patient continues the rate control medication. If AF is not present, at step 254 the patient is notified that AF has terminated and rate controlling medication therapy is to be terminated. In this example embodiment, for patients with chronic AF with accelerated (or breakthrough) fast ventricular response, PMS 118 alerts the patient to take an extra dose of rate control medication. If that dose is ineffective, or more than two extra doses are needed within a 24 hour to prevent a fast ventricular response, then the patient is notified to visit a physician.

In another embodiment, the antiarrhythmic, anticoagulation and ventricular rate control medication therapies guided by system 100 are simultaneously implemented. A patient that has an episode of AF is notified to take an antiarrhythmic medication in an attempt to terminate the arrhythmia. PMS 118 also notifies the patient that the ventricular response is in the fast zone and should also take a rate control medication. If no such therapies are successful and AF burden falls into the anticoagulation zone, the patient is notified to start anticoagulation therapy.

PMS 118 provides instructions to the patient on when medications and electrical therapies should be delivered based upon programmable features. The programmable features complement any device in the system that monitors, detects and notifies patient when an arrhythmia is occurring. Treatment options generated by PMS 118 include: 1) medications only and not implementing any electrical therapies, such as in the equipment sold under the brand Reveal™; 2) implementing pacing backup for drug-induced bardycardia; 3) implementing pacing backup with antitachycardia (AT500™); or 4) implementing pacing backup, antitachycardia pacing and defibrillation (Jewel AF™). PMS 118, in one embodiment, is a handheld device using standard telemetry communications protocols or a wristwatch device using radio frequency signals to establish the telemetry link with the IMD. The patient uses the handheld device upon receiving an audible notification tone (from PMS 118) to place the handheld device in close proximity to the IMD or an IPG (implanted pulse generator). The alphanumeric messaging circuit then instructs the patient regarding rhythm status and the type of medication or electrical therapies need to be administered. The patient also uses the handheld device to instruct the IPG as to when a medication was taken in order that electrical therapies are timed to occur at a maximal medication effect. Thus, any synergies between medication and electrical therapies are exploited.

Some of the advantages provided by the various embodiments of the present invention include: early recognition of the need for therapy; proper diagnosis and therapy early in the detection process; and reduced risk of toxicity from medications that would normally be taken chronically due to an inability to properly diagnose the heart condition. With the present invention, antiarrhythmic medications are administered when an atrial fibrillation occurs and the patient is not be burdened with the expense, toxicity and inconvenience of daily medication consumption. In addition, quantifying the daily AF burden and ventricular response can guide usage of anticoagulation and rate control drug. Moreover such diagnosis and patient awareness will document drug therapy efficacy on a real time basis. By diagnosing on a timely basis a patient's heart condition, such as an arrhythmia, undesirable consequences such as chronic AF, congestive heart failure or thromboembolic events can be avoided. Continuous monitoring of heart rhythm with patient notification of arrhythmia onset and termination will allow the patient to be in control of their AF management. With improved arrhythmia management provided by the present invention the patient is alerted to take medication, to deliver electrical therapy (pacing or defibrillation) or seek medical attention before onset of conditions requiring anticoagulation therapy.

FIG. 3 illustrates a system 300 for accessing and processing IMD patient diagnostic data, as well as formatting such data as a function of the IMD patient's request, in accordance with an example embodiment of the invention. The method and system facilitate the access by an IMD patient of diagnostic data for patient education and evaluation. IMD information is retrievable from and is displayable at a home environment 302, for example. Additional information is retrievable through a database located at a data processing center or hospital via the Internet 304. Patient information that is retrieved in a healthcare facility 306, and stored in a secured database, is accessible by the patient via the Internet 304 or by telephone or other communication systems.

In this example embodiment, the patient first establishes a communications link between the IMD and the IMD data processor 108 via the IMD device interface as in FIG. 1. A secured IMD database provided by the IMD data processor is then accessed using a set of patient identification data (e.g., IMD serial number or an alpha-numeric password assigned by database manager). A set of patient diagnostic data from IMD 102 is then transmitted via an uplink transmission to IMD data processor 108 for processing. A set of formatted data is generated, as a function of a request from the patient, by IMD data processor 108 using the patient's diagnostic data. In one example, current diagnostic data is compared with the patient's historical information stored in database 109. In another example, the data is also formatted to draw comparisons with information from other IMD users to illustrate a trend or for recognition of a pattern in the patient's IMD operation. The formatted data generated by IMD data processor 108 is then displayed for use in the patient's own evaluation or as an interactive tool to be used with the physician or with a data processing center having staff knowledgeable in implanted medical devices. In another embodiment, the interactive component is available for discussing the patient formatted data with a remotely located expert data center or physician. This can include a voice connection via a home PC or using the telephone to have a discussion concerning the displayed data.

As illustrated in FIG. 3, the patient diagnostic data is retrievable from the IMD and certain heart conditions are detectable by IMD data processor 108 (or PMS 118) that include, but are not limited to, Atrial Fibrillation, Ischemia, MI (Myocardial Infarction) and SCD (Sudden Cardiac Death) detection and prediction. Other equipment that can be incorporated into system 100 for improved diagnostic capability of a patient's IMD condition include: implanted event recorders, implanted diagnostic monitors and pacing/defibrillation systems. Other non-invasive physiological information can also be gathered by system 100 that would assist the patient in conducting a minimal level of self-health evaluation. For example, ECG information is retrievable for analysis by the patient well before a health condition occurs that requires hospitalization. This information is recorded in the database 109 for later use in patient diagnostic data analysis and is accessible through server 113 of communications network 112 or through the Internet 304.

Some of the advantages provided by the various embodiments of the present invention include enhanced patient availability for regular IMD and ECG evaluations and a comfortable interrogation session in a patient's home or familiar environment that eliminates the necessity of traveling to the hospital.

The present invention is compatible with a number of techniques for interrogating implanted medical devices, such as drug pumps, neurological implants, nerve stimulators, various cardiac implants and equivalent medical devices. In addition, the embodiments described are compatible with remote patient management systems that interact with remote data and expert data centers and compatible with a data communication system that enables the transfer of clinical data from the patient to a remote location for evaluation, analysis, data reposition, and clinical evaluation.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A method for patient participation in clinical care and therapy delivery in connection with detected heart conditions comprising:
    establishing a communications link between an implanted medical device and a data processor via an implanted medical device interface when an episode of a detected heart condition commences;
    obtaining access to a secured database via the data processor using a set of patient identification data;
    submitting via the data processor a query to the secured database in response to patient diagnostic data obtained from the implanted medical device wherein submitting the query comprises:
        detecting via the data processor at least one of a plurality of predefined conditions of the patient's implanted medical device; and
        generating a data response as a function of the detected conditions;
    providing a data response based upon the query and the patient diagnostic data including at least one of electrical impulse therapy and medication therapy; and
    displaying the data response in the form of a patient notification that an episode of a detected heart condition has occurred and guides the patient in actuation of the implanted medical device to invoke at least one of an electrical impulse therapy delivery and a medication therapy delivery in treatment of the episode of a detected heart condition;
    notifying the patient via the data processor of the detected condition;
    monitoring the implanted medical device; and
    displaying a first implanted medical device status
    displaying a first set of treatment options as a function of the first implanted medical device status and of the patient notification; and
    exercising at least one of the treatment options,
    wherein displaying treatment options includes displaying at least one medical option along with a time interval for exercising the displayed option.

2. The method of claim 1, wherein the step of detecting a condition includes the steps of:
    performing an uplink transmission of a set of patient diagnostic data from the implanted medical device to the data processor; and
    processing the patient diagnostic data to detect at least one of the plurality of conditions.

3. The method of claim 1, wherein the treatment options are selected from the group consisting of: medication, electrical impulse from the implanted medical device, and a request for medical assistance.

4. The method of claim 1, further comprising the step of notifying the data processor of the exercised treatment option.

5. The method of claim 4, further comprising the steps of:
    monitoring the implanted device continuously after notification of exercise of the displayed option; and
    notifying the patient of a second medical device status and of a second set of treatment options, the second set of treatment options being a function of the exercised option and the second medical device status.

6. The method of claim 4, further comprising the step of reconfiguring the treatment options as a function of the exercised option and the IMD status.

7. The method of claim 1, further comprising the step of reconfiguring patient notification of the detected condition such that the patient notification is responsive to a second plurality of conditions.

8. The method of claim 1, wherein obtaining access to the secured database includes obtaining access to a remotely located secured database via a communications network.

9. The method of claim 1, wherein the step of establishing a communications link includes automatically retrieving the set of patient identification data from the IMD.

10. The method of claim 1 wherein the patient diagnostic data includes patient cardiac condition data.

11. The method of claim 1 wherein the patient diagnostic data includes patient cardiac arrhythmia data.

12. The method of claim 1 wherein the patient diagnostic data includes patient atrial fibrillation data.

13. The method of claim 1 wherein the patient diagnostic data relates to at least one heart condition including Atrial Fibrillation, Ischemia, MI (Myocardial Infarction), and SOD (Sudden Cardiac Death).

14. The method of claim 1 wherein the patient is guided to activate a defibrillation mode of the implanted medical device to apply a shock to terminate an arrhythmia.

15. The method of claim 1 wherein the patient is guided to activate a pacing mode of the implanted medical device to terminate an arrhythmia.

16. The method of claim 1 wherein the patient is guided to administer an anti-arrhythmic medication in combination with the electrical impulse therapy delivery.

17. A system for patient participation in clinical care and therapy delivery in connection with an episode of a detected heart condition in a patient having an implanted medical device, comprising:
    a data processor having a database;
    an interface establishing a communications link between an implanted medical device and the data processor interface when an episode of a detected heart condition commences, the interface sending patient diagnostic data obtained from the implanted medical device and receiving a data response from the data processor based upon an analysis of the patient diagnostic data, wherein input patient diagnostic data includes an IMD patient request for information; and
    a patient messaging system coupled to the interface and displaying the data response received from the data processor in the form of a patient notification that an episode of a detected heart condition has occurred and that guides the patient in actuation of the implanted medical device to invoke at least one of an electrical impulse therapy delivery and a medication therapy delivery in treatment of the episode of a detected heart condition along with a time interval for exercising the actuation.

18. The system of claim 17 wherein the patient messaging system is coupled via a telemetry link to the implanted medical device and is adapted to access patient diagnostic data and independently alert the patient of a heart condition that requires some form of therapy or treatment.

19. The system of claim 17 wherein the interface is a programming unit and includes a programming head for accessing patient diagnostic data from the implanted medical device.

20. The system of claim 17 wherein the communication link established by the interface is one of a telephone connection, a video conference call connection, a cellular telephone connection, and an Internet connection.

21. The system of claim 17 further comprising a second communications link coupling the data processor to a communications network having a server and an expert data center.

22. The system of claim 17 wherein the patient messaging system is implemented within a personal digital assistant.

23. The system of claim 17 wherein the patient messaging system displays to the patient in real time a measure of the progress of an invoked therapy.

24. The system of claim 17 wherein the patient diagnostic data relates to a heart condition concerning at least one of a cardiac arrhythmia, tachycardia, and bradycardia.

25. The system of claim 17 wherein the patient messaging system displays a patient notification that guides the patient to activate a defibrillation mode of the implanted medical device to apply a shock to terminate an arrhythmia.

26. The system of claim 17 wherein the patient messaging system displays a patient notification that guides the patient to activate a pacing mode of the implanted medical device to terminate an arrhythmia.

27. The system of claim 17 wherein the patient messaging system displays a patient notification that guides the patient to activate an anti-arrhythmic medication delivery in combination with electrical impulse therapy delivery.

28. The method of claim 1 wherein input patient diagnostic data includes an IMD patient request for information from the secured database.

* * * * *

UNITED STATES PATENT AND TRADEMARK OFFICE
CERTIFICATE OF CORRECTION

| | |
|---|---|
| PATENT NO. | : 7,366,570 B2 |
| APPLICATION NO. | : 10/376061 |
| DATED | : April 29, 2008 |
| INVENTOR(S) | : Riff et al. |

It is certified that error appears in the above-identified patent and that said Letters Patent is hereby corrected as shown below:

Col. 12, line 33, delete "and SOD" and insert in place there of --and SCD--.

Signed and Sealed this

Sixth Day of January, 2009

JON W. DUDAS
*Director of the United States Patent and Trademark Office*